United States Patent [19]

Vanderheyden et al.

[11] Patent Number: 5,053,186

[45] Date of Patent: Oct. 1, 1991

[54] SOLUBLE IRRADIATION TARGETS AND METHODS FOR THE PRODUCTION OF RADIORHENIUM

[75] Inventors: Jean-Luc E. Vanderheyden; Fu-Min Su, both of Seattle, Wash.; Gary J. Ehrhardt, Columbia, Mo.

[73] Assignees: NeoRx Corporation, Seattle, Wash.; The Curators of the University of Missouri, Columbia, Mo.

[21] Appl. No.: 416,243

[22] Filed: Oct. 2, 1989

[51] Int. Cl.$^5$ .............................. G21G 1/00
[52] U.S. Cl. ................................. 376/189; 376/158; 250/432 PD; 423/2
[58] Field of Search ................. 376/158, 189; 423/2, 423/49; 250/432 PD

[56] References Cited

U.S. PATENT DOCUMENTS

| | | | |
|---|---|---|---|
| 3,324,005 | 6/1967 | Miller | 376/158 |
| 3,332,737 | 7/1967 | Kraus | 23/50 |
| 4,278,641 | 7/1981 | Petrov et al. | 423/49 |
| 4,280,053 | 7/1981 | Evans et al. | 250/432 PD |
| 4,738,834 | 4/1988 | Moore et al. | 423/2 |
| 4,778,672 | 10/1988 | Deutsch et al. | 424/1.1 |
| 4,839,467 | 6/1989 | Deutsch | 534/10 |
| 4,859,431 | 8/1989 | Ehrhardt | 423/2 |
| 4,990,787 | 2/1991 | Vanderheyden et al. | 250/432 PD |

FOREIGN PATENT DOCUMENTS 3675 2/1978 Australia.

OTHER PUBLICATIONS

M. B. Varfolomeey et al., "Aluminium and Gallium Perrhenate Heptahydrates", *Russian Journal of Inorganic Chemistry* 14(1), 35-38, 1969.
L. L. Zaitseva et al., "Physicochemical Properties of Aluminium Pertechnetate and Aluminium Perrhenate", *Russian Journal of Inorganic Chemistry* 31(6), 816-818, 1986.
Evans, J. et al., "Zirconium Molybdate Gel as a Generator for Technetium-99m—I. The Concept and its Evaluation", *Appl. Radiat. Isot.* 38(1), 19-23, 1987, *Int. J. Radiat. Appl. Instrum. Part A*.
Moore, P. W. et al., "Zirconium Molybdate Gel as a Generator for Technetium-99m—II. High Activity Generators", *Appl. Radiat. Isot.* 38(1), 25-29, 1987, *Int. J. Radiat. Appl. Instrum. Part B*.
Blachot, J. et al., "Un Generateur de $^{188}$Re a Partir de $^{188}$W", *International Journal of Applied Radiation and Isotopes* 20, 467-470, 1969.
Kordyukevich, V. O. et al., "Extractive Separation of Rhenium Isotopes Without Carriers from a Tungsten Target", *Radiokhimya* 26(5), 625-629, 1984.
Evans, J. V. et al., "A New Generator for Technetium-99m", purportedly presented at 3rd World Congress Nuclear Medicine & Biology, Paris, Aug. 1982.
Narasimhan, D. V. S. et al., "A New Method for $^{99m}$Tc Generator Preparation", *J. Radioanal. Nucl. Chem. Letters* 85(6), 345-355, 1984.
Narasimhan, D. V. S. et al., "Preparation of a Sterile Closed System $^{99m}$Tc Generator Based on Zirconium Molybdate", *J. Radioanal. Nucl. Chem. Letters* 85(3), 163-172, 1984.
Boyd, R. E., "Technetium-99m Generators—The Available Options", *Int. J. Appl. Radiat. Isot.* 33, 801-809, 1982.
Deutsch, E. et al., "The Chemistry of Rhenium and Technetium as Related to the Use of Isotopes of these Elements in Therapeutic and Diagnositc Nuclear Medicine", *Nucl. Med. Biol.* 13(4): 465-477, 1986, *Int. J. Radiat. Appl. Instrum., Part B.*
Britton, H. T. S. and German, W. L., "CXCIII.—Physicochemical Studies of Complex Acids. Part VI. The Precipitation of Molybdates", pp. 1429-1435, 1931.
Ryabchikov, D. et al., "Chromatographic Separation of Rhenium from Molybdenum and Tungsten by Means of Mixed Eluents on EDE-10 Anion Exchange Resin", translated from *Zhurnal Analiticheskol Khimii* 17, 890-892, 1962.
Pinagian, J., "A Technetium-99m Generator Using Hydrous Zirconium Oxide", *Internatl. J. of Applied Radiation and Isotopes* 17, 664-666, 1966.

(List continued on next page.)

Primary Examiner—Daniel D. Wasil
Attorney, Agent, or Firm—Christensen, O'Connor, Johnson & Kindness

[57] ABSTRACT

Water soluble irradiation targets are disclosed for the production of $^{186}$Re and $^{188}$Re. The irradiation targets are selected for both water solubility and absence of elements which would produce contaminating isotopes for medical therapeutic and diagnostic use. In one embodiment, $^{186}$Re or $^{188}$Re is produced by the direct irradiation of a water soluble irradiation target comprising $^{185}$Re or $^{187}$Re, respectively. Preferred targets for this purpose include aluminum perrhenate, lithium perrhenate and magnesium perrhenate. In another embodiment, a zirconyl tungstate generator comprising $^{188}$W for the production of $^{186}$Re is obtained by irradiating a soluble irradiation target comprising $^{186}$W, dissolving the irradiated target in aqueous solution, reacting the dissolved target with an aqueous solution comprising zirconyl ion to form an insoluble zirconium tungstate precipitate and disposing the precipitate in an elutable container. Preferred irradiation targets for this purpose include sodium tungstate and lithium tungstate. In each of the foregoing embodiments, the irradiation target is readily soluble in aqueous solution and may be used directly in solution form after irradiation, such as for ligand conjunction for medical diagnostic or therapeutic purposes, without cumbersome dissolution, neutralization, purification and other processing steps involving irradiated materials inherent in prior $^{186}$Re and $^{188}$Re production methods.

7 Claims, No Drawings

OTHER PUBLICATIONS

Plotnikov, V. et al., "Separation of Small Amounts of Rhenium and Tungsten by Means of Zirconium Hydroxide", translated from *Zhurnal Analiticheskol Khimii* 21, 1260–1262, 1966.

Lewis, R. et al., "Production of 70-Day Tungsten-188 and Development of a 17 Hour Rhenium-188 Radioisotope Generator", *J. Nucl. Med.* 7, 804–805, 1966.

Meloni, S. et al., "A New Technetium-99m Generator Using Manganese Dioxide", *Internatl. J. of Applied Radiation and Isotopes* 19, 164–166, 1968.

Klofutar, C. et al., "Radiochemical Separation of Rhenium (VII) from Tungsten (VI)", *Journal of Radioanalytical Chemistry* 5, 3–10, 1970.

Malyshev, K. V. et al., "Generator of Rhenium-188 Based on Hydrated Zirconium Oxide", translated from *Radiokhimiya* 17, 249–251, 1975.

Tanase, M., "Separaton of $^{99m}$Tc from Neutron-Irradiated $MoO_3$ by Precipitation as $CaMoO_4$", *Journal of Radioanalytical Chemistry* 41, 23–27, 1977.

Ehrhardt, G. J. et al., abstract No. 416 entitled, "An Improved Tungsten-188/Rhenium-188 Generator for Radiotherapeutic Applications", *Journal of Nuclear Medicine* (Proceedings of the 34th Annual Meeting), 28(4), 656–657, 1987.

SOLUBLE IRRADIATION TARGETS AND METHODS FOR THE PRODUCTION OF RADIORHENIUM

FIELD OF THE INVENTION

The present invention relates to the field of neutron irradiation for the production of radionuclides useful for medical therapeutic and diagnostic purposes. More particularly, this invention relates to improved irradiation targets for the production of rhenium-186 and rhenium-188.

BACKGROUND OF THE INVENTION

Isotopes of rhenium have recently become of interest to the nuclear medicine community for use in diagnostic and therapeutic applications. Two isotopes of rhenium, $^{186}$Re and $^{188}$Re, are of particular significance due to their suitability for therapeutic and diagnostic applications. Both $^{186}$Re and $^{188}$Re are $\beta$-emitting radionuclides (beta energies of 1.07 and 2.12 Mev, respectively) with relatively short half lives (90 hours for $^{186}$Re and 16.98 hours for $^{188}$Re). In addition, both exhibit gamma emissions (9.2%, 137 kev and 15%, 155 kev, respectively) suitable for gamma counter imaging of biodistribution in vivo.

$^{186}$Re is conventionally produced from $^{185}$Re (37% natural abundance) by neutron capture in a nuclear reactor. The nuclear properties of this isotopic system are as follows:

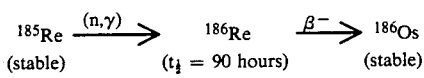

In the production of $^{186}$Re, rhenium-185 metal is typically irradiated at a high flux rate, such as at $10^{14}$–$10^{15}$ neutrons/cm$^2$/s, for periods of 24 hours or more. After irradiation, the resulting $^{186}$Re isotope must be solubilized for clinical applications, such as for conjugation to tumor-specific antibodies, typically by treatment with a strong oxidizing agent, e.g., hydrogen peroxide or concentrated nitric acid, to obtain a soluble perrhenate solution. The perrhenate solution, containing $^{186}$Re, must then be neutralized and purified to remove contaminants prior to antibody conjugation and/or other clinical applications.

$^{188}$Re is conventionally derived from either natural rhenium-187 (63% natural abundance) in carrier-added form by neutron bombardment in a nuclear reactor or, preferably, in high specific activity, carrier-free form from a generator made of a target tungsten material, enriched in $^{186}$W, by double neutron capture in a high-flux reactor to produce $^{188}$W and its decay product $^{188}$Re. The nuclear properties of this isotopic system are as follows:

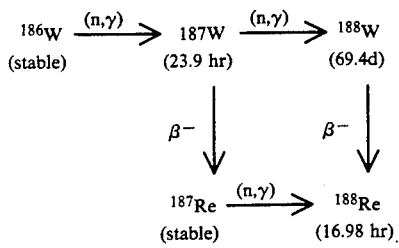
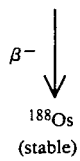

Since $^{188}$Re produced from neutron capture by irradiation of $^{187}$Re is accompanied by unconverted $^{187}$Re and other impurities (i.e., is obtained in carrier added form) and since the short half-life of $^{188}$Re limits the efficiency of $^{188}$Re accumulation during relatively longer-term irradiation and subsequent handling procedures, the production of $^{188}$Re by nuclear decomposition in no carrier added form in a tungstate/rhenium generator system is highly preferred.

Previous tungsten/rhenium generators for the production of $^{188}$Re have consisted of small, alumina columns with relatively small amounts of tungsten targets adsorbed on the columns and, thus, low rhenium yields in the microcurie ($\mu$Ci) range. To increase the amount of rhenium obtainable from such columns (i.e., in the millicurie range, mCi), larger column masses are necessary in order to contain larger amounts of target tungsten. These larger columns, in turn, require increased eluting volumes. In addition, prior $^{188}$W/$^{188}$Re generators using alumina columns have provided poor yields of $^{188}$Re and unacceptable levels of release, or "breakthrough", of $^{188}$Re from the column due primarily to the necessity of adsorbing large (0.5–2.0 grams) amounts of target tungsten (primarily as $^{186}$W) onto the alumina column.

U.S. Pat. No. 4,859,431 of Ehrhardt discloses an improved $^{188}$Re generator in which an insoluble zirconyl tungstate matrix containing $^{188}$W decays over time producing $^{188}$Re in the form of perrhenate ($^{188}$ReO$_4^-$), which is readily elutable from the matrix. The zirconyl tungstate matrix as disclosed in the Ehrhardt patent is produced by dissolving irradiated tungsten trioxide in a heated basic solution, adding the basic tungsten trioxide solution to an acidic zirconium-containing solution to obtain an acidic zirconyl tungstate slurry containing $^{188}$W, drying the slurry to form a permeable matrix, and then packing the matrix in an elutable column. The Ehrhardt generator has been found to be a highly effective generator of $^{188}$Re.

Although the direct irradiation of $^{185}$Re has proven effective for the production of $^{186}$Re, and both the direct irradiation of $^{187}$Re and the zirconyl tungstate generator system have proven to be effective for the production of $^{188}$Re, these systems have inherent drawbacks which limit their large-scale use and acceptability. In the case of direct irradiation of $^{185}$Re or $^{187}$Re, the irradiated $^{186}$Re or $^{188}$Re in the form of rhenium metal or rhenium trioxide must be solubilized, typically by oxidation with concentrated nitric acid, to form soluble perrhenate (ReO$_4^-$). The perrhenate solution must then be neutralized, such as with aqueous ammonia. This procedure not only is time consuming and requires extensive handling and processing of irradiated materials, but also results in unwanted by-products which must be separated from the perrhenate. Prior tungsten/rhenium generator systems for the production of $^{188}$Re also require significant handling and processing of irradiated materials, including dissolution, precipitation, filtration, drying, gel fragmentation and column packing steps, all occurring after irradiation of the tungsten metal or tungsten trioxide starting materials. These processing steps with irradiated materials necessitate the use of cumbersome shielded processing equipment, result in relatively high manufacturing costs and pose significant potential safety risks.

U.S. Pat. No. 4,778,672 of Deutsch et al. discloses a procedure for the purification of irradiated perrhenate and tungstate solutions, primarily to eliminate contaminants introduced through harsh conditions required for target dissolution. In the Deutsch et al. procedure, irradiated rhenium metal is dissolved by the addition of concentrated nitric acid and the resulting solution is neutralized with ammonia. The neutralized solution, containing solubilized perrhenate, is then treated with a soluble lipophilic counter ion, such as a solution of tetrabutyl ammonium bromide, and passed through a preferential sorption column, which has been pretreated with the counter ion, to separate the perrhenate from the solution. The retained perrhenate, which has been separated from unwanted by-products formed in the rhenium dissolution process, is then eluted from the column. The foregoing procedure may also be employed in the purification of pertechnetate eluant obtained from a molybdenum-99/technetium-99m generator column or perrhenate eluant from a tungsten-188/rhenium-188 generator column. The process of the Deutsch patent has been found to be effective for the removal of impurities from pertechnetate and perrhenate solutions. This process, however, is time consuming and further aggravates the costs and other problems associated with processing of irradiated materials. These problems remain particularly acute in connection with the production of $^{186}$Re which, due to its relatively short half-life and production by direct irradiation, must frequently be processed into suitable form on-site in a clinical or hospital setting.

In order to avoid some processing steps with irradiated materials in connection with the generator production of $^{99m}$Tc in a related molybdenum/technetium generator system, Narasimhan et al., "A New Method for $^{99m}$Tc Generator Preparation," *J. Radioanal. Nucl. Chem.*, Letters, Vol. 85, No. 6, pp. 345–356, discloses an improved method of preparing a zirconium molybdate $^{99m}$Tc generator in which the precipitation, filtration, drying and fragmentation of radioactive materials required in the preparation of a zirconium molybdate $^{99m}$Tc generator are avoided by directly irradiating zirconium molybdate instead of molybdenum trioxide as in prior zirconium molybdate generator systems. However, the direct irradiation of zirconium molybdate as reported by Narasimhan et al. resulted in the production of radioactive contaminants unacceptable for clinical therapeutic or diagnostic applications, including $^{97}$Zr, $^{95}$Zr, $^{175}$Hf, $^{181}$Hf, and $^{24}$Na.

Thus, a strong need exists for improved irradiation targets for the production of $^{186}$Re and $^{188}$Re which will simplify the dissolution of these radionuclides or their precursors and reduce the handling procedures, costs and safety hazards associated with their production in a form suitable for medical diagnostic or therapeutic use.

SUMMARY OF THE INVENTION

It has now been discovered that the foregoing problems associated with the conventional production of $^{186}$Re and $^{188}$Re can be significantly reduced by the direct irradiation of specific water soluble irradiation targets, which are selected for both water solubility and absence of elements which would produce contaminating isotopes for medical therapeutic and diagnostic use. In one embodiment of the invention, $^{186}$Re is produced by the direct irradiation of a water soluble irradiation target comprising $^{185}$Re. Presently preferred targets for this purpose include aluminum perrhenate, lithium perrhenate and magnesium perrhenate. In another embodiment of the invention, soluble aluminum perrhenate, lithium perrhenate or magnesium perrhenate comprising $^{187}$Re may be directly irradiated for the production of $^{188}$Re. In yet another embodiment of the invention, a zirconyl tungstate generator comprising $^{188}$W for the production of $^{188}$Re is obtained by irradiating a soluble irradiation target comprising $^{186}$W, dissolving the irradiated target in aqueous solution, reacting the dissolved target with an aqueous solution comprising zirconyl ion to form an insoluble zirconium tungstate precipitate and disposing the precipitate in an elutable container. Presently preferred irradiation targets for this purpose include sodium tungstate and lithium tungstate. In each of the foregoing embodiments, the irradiation target is readily soluble in aqueous solution and may be used directly in solution form after irradiation, such as for ligand conjunction for medical diagnostic or therapeutic purposes, without cumbersome dissolution, neutralization, purification and other processing steps involving irradiated materials inherent in prior $^{186}$Re and $^{188}$Re production methods.

DETAILED DESCRIPTION OF THE INVENTION

The present invention provides improved rhenium irradiation targets for use in the production of the radionuclides $^{186}$Re and $^{188}$Re. Suitable irradiation targets for use in the invention are selected both for their water solubility and the absence of elements which would produce contaminating isotopes upon irradiation which would interfere with the use of the desired radionuclides $^{186}$Re or $^{188}$Re for medical therapeutic or diagnostic purposes. As used herein, the term "soluble" means a compound having a relatively high degree of solubility in water. The soluble irradiation targets of the invention will generally have a degree of solubility in water of at least about 1,000 grams per liter, and more preferably at least about 3,000 grams per liter. In addition, the irradiation targets are selected for the absence of elements that, upon irradiation, would produce radioisotopes which would interfere or otherwise contaminate the desired $^{186}$Re or $^{188}$Re radionuclides.

Presently preferred soluble irradiation targets for use for direct irradiation in the production of $^{186}$Re or $^{188}$Re include aluminum perrhenate, lithium perrhenate and magnesium perrhenate. The presently most preferred soluble irradiation target for this purpose is aluminum perrhenate. When the desired radionuclide is $^{186}$Re, the irradiation target will preferably be enriched in $^{185}$Re. Similarly, when the desired radionuclide is $^{188}$Re, the target will preferably be enriched in $^{187}$Re. When lithium perrhenate is used as an irradiation target, the target will additionally be enriched in $^7$Li to avoid undesirable by-products, e.g., tritium, associated with neutron capture by $^6$Li. For purposes of use in a tungsten/rhenium generator comprising $^{188}$W for the production of $^{188}$Re, presently preferred targets include sodium tungstate and lithium tungstate, with sodium tungstate being presently most preferred. Particularly preferred targets for this purpose will be enriched in $^{186}$W, and when comprised of lithium, will additionally be enriched in $^7$Li.

The soluble irradiation targets of the invention may be obtained by the dissolution of rhenium metal, tungsten metal, or rhenium or tungsten trioxides by processes well known in the art. For example, rhenium metal may be dissolved in concentrated nitric acid or a hydrogen peroxide solution, and tungsten metal may be dissolved in concentrated nitric acid and hydrofluoric acid. The acidic mixture may then be taken to dryness to volatilize undesirable components, such as HF (when present), and reconstituted in water. The resulting solution, containing perrhenate or tungstate, may be mixed with an aqueous solution of the desired counter ion. The solution may then be heated to dryness to recover the soluble irradiation target in dry form. If desired, the irradiation target may be redissolved, such as in water, further purified, such as by filtration, and then heated to dryness, in one or more washing steps to further purify the target. Recovered solid material may then be directly irradiated in a neutron reactor in a conventional manner.

In another aspect of the invention, an improved method is provided for the production of the radionuclides $^{186}$Re or $^{188}$Re, comprising irradiating a water soluble irradiation target comprising $^{185}$Re or $^{187}$Re, respectively, and then dissolving the irradiated target in an aqueous solution. By directly irradiating the water soluble irradiation target, as opposed to the irradiation of rhenium metal or trioxide in conventional processes, the cumbersome purification, processing and handling procedures of irradiated materials inherent in prior art rhenium radionuclide production processes are substantially reduced.

In another aspect of the invention, an improved process for producing a tungsten/rhenium generator for the production of $^{188}$Re is provided which comprises irradiating a soluble target selected from sodium tungstate or lithium tungstate comprising $^{186}$W to obtain an irradiated soluble tungstate salt, comprising $^{188}$W, reacting the soluble tungstate salt with an aqueous zirconium solution to obtain an insoluble zirconium tungstate gel or matrix, and then disposing the zirconium tungstate gel in an elutable container. Production of the generators of the invention provides significant advantages over prior art processes for the production of zirconyl tungstate gel matrix-type generator systems, since the soluble irradiation target may be directly irradiated, readily solubilized, reacted with zirconium ion to form an insoluble zirconium tungstate gel and then packed into a column, thereby avoiding the cumbersome nitric acid and hydrofluoric acid dissolution, purification and other processing steps with irradiated materials required in the prior art generator system production processes. The soluble irradiation target is preferably dried to solid form providing a convenient form for direct irradiation. After irradiation, $^{187}$W (half-life, 24 hours) and $^{24}$Na (half-life, 15 hours), when present, are preferably allowed to decay from the irradiated materials, and the irradiated target is readily dissolved in water, insolubilized, such as by reaction with zirconyl nitrate, packed in a column and allowed to decay to form highly soluble ions comprising $^{188}$Re, typically in the perrhenate ($^{188}$ReO$_4^-$). The $^{188}$ReO$_4^-$ may then be readily eluted from the column.

In this generator embodiment, the zirconium tungstate matrix may be transferred to an empty container for eluting and harvesting of perrhenate containing $^{188}$Re. Suitable containers may include, for example, a glass column such as those used in standard chromatography encased in a "shell" including appropriate lead shielding, associated plumbing and a reservoir of eluant to form a generator assembly. Alternatively, a separate sterile reservoir may be supplied for each series of elutions. It is desirable, but not essential, to keep the matrix hydrated at all times. Periodically, the daughter radionuclide is conveniently eluted from the column using a suitable eluant solution, such as water or saline. A presently particularly preferred eluant solution is physiological saline.

Performance of an improved generator of the present invention may be expressed as elution efficiency. Elution efficiency may be calculated by measuring the amount of radioactivity of the daughter radionuclide present in the eluant divided by the amount of radioactivity of the daughter radionuclide originally present on the generator column, immediately prior to elution. The radioactivity of the radionuclide may be determined using standard instruments for measuring radioactivity including gamma ray spectrophotometers such as germanium detectors and sodium iodide scintillation spectrophotometers, which are capable of measuring low levels of radioactivity, or dose calibrators that can measure high levels of radioactivity. In the present invention, since the generator consists of a small column, the entire column may be placed in a dose calibrator to directly measure the radioactivity of daughter radionuclide on the column before elution, and by subtracting from this value the amount of radioactivity of the daughter radionuclide on the column after elution, the amount of radioactivity of the radionuclide present in the eluant may be determined. This procedure provides a close approximation of the daughter radionuclide present in the eluant because, at the appropriate setting on the dose calibrator, the radioactivity measured on the column may be attributed to daughter radionuclide. Elution efficiencies are typically measured after approximately 3 to 10 daughter radionuclide half-lives. Elution efficiencies as high as 55%–65% may be obtained using the generators of the present invention, with concentrations of $^{188}$Re in the eluant of up to 30 mCi/ml and higher, determined immediately after elution and typically after 3 or 4 half-lives.

The radiochemical purity of the daughter radionuclide may be assessed using ion exchange, reversed phase high-performance liquid chromatography (HPLC) or scintillator chromatography using nonradioactive perrhenate as a standard.

During the elution process, a certain amount of the parent radionuclide may be released into the eluant, for example, in the form of small particles of the zirconium tungstate, causing contamination of the daughter radionuclide. A porous glass or plastic structure, such as a fritted glass disc used in chromatography columns, may be used to retain some of these particles to prevent entry of tungsten into the eluate. However, the amount of parent radionuclide released from the column is relatively low using the process of this invention (as low as 0.01%), since a large fraction of the generator matrix would have to dissolve before a substantial fraction of the parent radionuclide contained in it is released. Moreover, the level of parent radionuclide present in the eluate may be reduced by several orders of magnitude using a substrate which is capable of adsorbing the parent radionuclide, such as an alumina column or zirconium hydroxide bed, to purify the solution eluted from the generator. Thus, the generator system of the present invention may include a second elutable container, such as chromatographic column enclosing a second matrix containing such a tungsten-specific matrix, for removing any released $^{188}W$, in addition to the container enclosing the generator matrix. Alternatively, the substrate which is capable of adsorbing tungsten may be incorporated into the generator column, for example, below the zirconium tungstate matrix, so that the eluant passes through the substrate after first flowing through the tungstate matrix. An additional advantage of the use of the tungsten-adsorbing substrate is that the loss of small particles of matrix may be minimized, which in turn decreases the amount of eluted fluid containing such contamination particles which must be disposed of.

$^{188}W/^{188}Re$ generator devices made according to the present invention are quite compact and may be made using small masses of generator matrix. Since the $^{188}W$ can be produced at a specific activity of approximately 1 Curie (Ci)/gram or higher by neutron capture, it is apparent that small (Curie size) generator columns containing volumes as low as 5 ml may be constructed using this process.

The foregoing may be better understood in connection with the following representative examples which are presented for purposes of illustration, not limitation, of the inventive concepts.

EXAMPLES

EXAMPLE 1

Preparation of Aluminum Perrhenate Soluble Irradiation Target

Procedure No. 1.

0.1 ml concentrated nitric acid was carefully pipetted into a beaker containing 50 mg rhenium metal. After two to three minutes, 0.1 ml 1:1 v/v concentrated nitric acid:water solution was added to the reaction mixture, and the mixture was allowed to react at room temperature for 20 minutes. 0.5 ml water was added to the mixture, followed by the addition of 0.2 ml of a 0.447M aluminum chloride solution. The mixture was heated to dryness at 95° C. for 12 hours. 1 ml water was added to the beaker to dissolve the residue solid, then the solution was filtered. The filtrate was heated to dryness at 95° C. for 12 hours to yield a white solid, aluminum perrhenate. The elemental analysis of Al and Re is shown in Table I.

Procedure No. 2.

To 50 mg rhenium metal was carefully added 0.5 ml 30% $H_2O_2$ solution. After 10 minutes, 0.5 ml water was added to the mixture and the mixture was heated for 30 minutes at 95° C. 0.2 ml of 0.447M aluminum chloride solution was added to the mixture, and the mixture was heated to dryness at 95° C. for 12 hours. 1 ml water was added to dissolve the solid, then the solution was filtered. The filtrate was heated to dryness at 95° C. for 12 hours to obtain a white solid, aluminum perrhenate.

Procedure No. 3.

To 50 mg rhenium metal was carefully pipetted 0.1 ml concentrated nitric acid. After two to three minutes, 0.1 ml 1:1 v/v concentrated nitric acid:water solution was added to the reaction mixture, and the mixture was allowed to react at room temperature for 20 minutes. 0.1 ml ammonium hydroxide (conc.) was added to the reaction mixture, followed by the addition of 0.5 ml water. The mixture was heated at 95° C. until all solids had dissolved, and then 0.2 ml of 0.447M aluminum chloride solution was added to the mixture. The solution was heated to dryness at 95° C. for 12 hours. 1 ml water was then added to dissolve the solid, and the solution was filtered. Finally, the filtrate was heated to dryness at 95° C. for 12 hours to yield a white solid, aluminum perrhenate.

Procedure No. 4.

The procedure of Procedure No. 1 was followed, except 50 mg enriched Re-185 rhenium metal (95% Re-185, Isotec, Inc., Dayton, Ohio) was used in place of the natural occurrence rhenium metal of Procedure 1.

Procedure No. 5.

The procedure of Procedure No. 2 was followed, except 75 mg enriched Re-185 rhenium metal (95% Re-185, Isotec, Inc., Dayton Ohio) and 0.3 ml 0.477M aluminum chloride solution was used in place of the natural occurrence rhenium metal and aluminum chloride solution of Procedure 2.

Procedure No. 6.

The procedure of Procedure No. 3 was followed, except 50 mg enriched Re-185 rhenium metal (95% Re-185, Isotec, Inc., Dayton, Ohio) was used in place of the natural occurrence rhenium metal of Procedure 3.

The products of Procedure Nos. 1-6 were dissolved in 2 ml of water, diluted 1:200 in water, analyzed for rhenium and aluminum content and found to contain the amounts of rhenium and aluminum shown in the following Table 1 as μg per ml of sample.

TABLE I

| | Elemental Content (μg/ml) Procedure Number | | | | | |
|---|---|---|---|---|---|---|
| | #1 | #2 | #3 | #4 | #5 | #6 |
| Al | 5.0 | 5.2 | 5.4 | 5.1 | 7.6 | 4.5 |
| Re-total | 125.8 | 116.7 | 131.4 | 104.6 | 157.4 | 103.6 |
| Re-185 | 46.1 | 42.6 | 48.1 | 97.7 | 148.4 | 97.5 |
| Re-187 | 79.7 | 74.1 | 83.2 | 7.2 | 9.0 | 6.1 |
| Re—Al ratio | 25.2 | 22.4 | 24.3 | 20.5 | 20.7 | 23.0 |

EXAMPLE II

Irradiation of Soluble Aluminum Perrhenate Targets 0.24 mg samples of aluminum perrhenate produced by Procedures 4, 5 and 6 of Example 1 were placed in quartz irradiation vials, which were sealed by flame under vacuum. The vials were irradiated in a flux of $3 \times 10^{14}$ neutrons/cm$^2$/sec at the University of Missouri Research Reactor (Columbia, Mo.) for a period of 12-14 days. The vials were then opened and the irradiated aluminum perrhenate was dissolved in 0.5 ml of water. The average activity recovery was found to be greater than 90%, and the activity was identified as $^{186}Re$ (by germanium-lithium analyzer) in the form of $^{186}ReO_4^-$ (by reverse phase HPLC).

EXAMPLE III

Preparation of Sodium Tungstate Target 0.5 ml of a 5N NaOH solution was added to 0.2 g of $^{186}WO_3$ (96% $^{186}W$, Oak Ridge National Laboratory, Oak Ridge, Tenn.) in a 5 ml beaker, and the mixture was heated to dissolve the $^{186}WO_3$ material. After dissolution was complete, the mixture cooled to room temperature and adjusted to pH 9 by the addition of 5N HCL and 1N HCl. The solution was heated to dryness to obtain 0.292 g of a white solid, comprising sodium tungstate.

EXAMPLE IV

Irradiation of Soluble Sodium Tungstate Target

A 20 mg sample of sodium tungstate (W-186) prepared by the procedure of Example III was placed in a quartz irradiated vial, which was sealed by flame under vacuum. The vial was irradiated in a flux of $3 \times 10^{14}$ neutrons/cm$^2$/sec at the University of Missouri Research Reactor (Columbia, Mo.), for a period of seven days. $^{187}$W and $^{24}$Na were allowed to decay from the irradiated material. The vial was then opened and the irradiated sodium tungstate was dissolved in 1 ml of water. The solution was then filtered through a 0.2 μm filter. The activity recovery was determined to be greater than 95%.

EXAMPLE V

Preparation of Zirconium Tungstate Generator 40 mg of irradiated sodium tungstate prepared as described in Example IV was dissolved in 2 ml of water and filtered through a 0.2 μm filter. To the filtered solution 200 mg of natural occurrence Na$_2$WO$_4$ in 4 ml H$_2$O was added to aid in precipitation of insoluble tungstate. The tungstate solution was then added drop by drop to an acidic zirconyl solution containing 312 mg ZrO(NO$_3$)$_2$ in 6 ml of HCl solution, pH 1. The pH of the resulting zirconium tungstate mixture was 6.0. The mixture was then filtered and washed with 50 ml of water. The gel precipitation yield (percentage of $^{188}$W initially present which is complexed in the gel) was greater than 95%. The filtered gel was air dried overnight, packed into a conventional generator column, and eluted with physiological saline. The zirconyl tungstate generator was determined to have an elution yield of 66%.

While the invention has been described in connection with various presently particularly preferred embodiments, various modifications will be apparent to those skilled in the art. Any such modifications are intended to be within the scope of the appended claims, except insofar as precluded by the prior art.

What is claimed is:

1. A method of producing a rhenium-186 or rhenium-188 radionuclide for therapeutic or diagnostic use, comprising:
    irradiating a water soluble irradiation target selected from the group consisting of aluminum perrhenate, lithium perrhenate and magnesium perrhenate, to obtain the radionuclide or a parent isotope of the radionuclide, and
    dissolving the irradiated target in aqueous solution.

2. The method of claim 1 wherein the radionuclide is $^{186}$Re and the irradiation target comprises enriched $^{185}$Re.

3. The method of claim 2 wherein the irradiation target comprises enriched $^{7}$Li in the form of lithium perrhenate.

4. The method of claim 1 wherein the radionuclide is $^{188}$Re and the irradiation target comprises enriched $^{187}$Re.

5. A method for producing rhenium-186, comprising irradiating a water soluble irradiation target selected from the group consisting of aluminum perrhenate, lithium perrhenate and magnesium perrhenate, and dissolving the irradiated target in aqueous solution.

6. The method of claim 5 wherein the irradiation target is enriched in rhenium-185.

7. The method of claim 6 wherein the irradiation target is aluminum perrhenate.

* * * * *